United States Patent [19]

Ogushi et al.

[11] Patent Number: 5,976,376
[45] Date of Patent: Nov. 2, 1999

[54] SEWAGE TREATMENT PROCESS

[75] Inventors: Yasuyuki Ogushi; Masato Kaneko; Naohiko Ukawa; Susumu Okino; Masao Hino; Takashi Haruki, all of Hiroshima-ken; Taku Shimizu; Kiyoshi Okazoe, both of Tokyo; Masaharu Yoshimi, Kanagawa-ken, all of Japan

[73] Assignee: Mitsubishi Jukogyo Kabushiki Kaisha, Tokyo, Japan

[21] Appl. No.: 08/745,302

[22] Filed: Nov. 8, 1996

[51] Int. Cl.$^6$ ....................................................... C02F 3/34
[52] U.S. Cl. ........................ 210/611; 210/912; 435/262.5; 435/874; 588/223
[58] Field of Search ..................................... 210/610, 611, 210/912; 435/262.5, 874–877; 588/215, 223

[56] References Cited

U.S. PATENT DOCUMENTS

| | | | |
|---|---|---|---|
| 4,519,913 | 5/1985 | Baldwin et al. | 210/611 |
| 4,725,357 | 2/1988 | Downing et al. | 210/611 |
| 4,910,010 | 3/1990 | Khalafalla | 210/611 |

*Primary Examiner*—Thomas G. Wasyne
*Attorney, Agent, or Firm*—Michael N. Meller

[57] ABSTRACT

A process for the treatment of sewage to provide effective removal of selenium (especially the 6-valent selenium) to meet required standards for the dissolved amount of selenium, and the like, at a low cost are developed. The process and apparatus reduces selenium from the 6-valent selenium using microbiological treatment to obtain 4-valent selenium and/or simple selenium, and then provide a solid-liquid separation.

4 Claims, 2 Drawing Sheets

SEWAGE TREATMENT PROCESS

BACKGROUND OF THE INVENTION

This invention claimed hereafter is related to a process and apparatus developed for sewage treatment. More particularly, it is about a sewage treatment process and apparatus in which selenium (Se), specifically the 6-valent selenium, is effectively removed from sewage containing selenium.

In general, a wet-type flue gas desulfurization system is widely used for power-generating facilities, etc. In such flue gas desulfurization system smog is generally contacted with an absorbent slurry (e.g., limestone slurry). Sulfur oxides are then absorbed while the formed gypsum is separated from the slurry in the absorber as a by-product. However, sewage discharged from such flue gas desulfurization system can contain hazardous materials carried over from the smog and dissolved in the sewage. The hazardous materials must be removed from the sewage before it is discharged or recycled. Particularly, sewage from flue gas desulfurization system used for a coal boiler has a maximum selenium content of 10 milligrams per kg. coal, currently causing an environmental problem. Therefore, in order to provide harmless sewage discharges, it is desired that the sewage is treated to have its selenium content removed.

Note that selenium has a toxicity similar to arsenic compounds. Therefore, reports about disabilities cases have brought about imposition of emission regulations overseas. In Japan, since February 1994, selenium has become a newly regulated item, in conformity with the following standard: 0.01 milligram per liter under the environmental standard, 0.1 milligram per liter under the emission standard, and 0.3 milligram per liter under the standard for the amount precipitated into reclaimed land. In addition, selenium exists in the 4-valent state (primary form: selenious acid $SeO_3^{2-}$) and in the 6-valent state (primary form: selenic acid $SeO_4^{2-}$). It should be noted that the 6-valent selenium has a high solubility (95% at 20° C.) and dissolves easily in water.

Actual flue gas desulirization systems are equipped with sewage treatment apparatus in which the sewage is cleaned. However, the conventional sewage treatment apparatus uses a process consisting of aggregation and precipitation, COD (Chemical Oxygen Demand) treatment, and denitrification treatment using microorganisms, respectively. Treatment for the reduction of selenium is not considered.

Conventional process for the removal of 4-valent selenium contained in water and the like is available. In this process the 4-valent selenium is separated (solvent extraction) into solid and liquid by means of treatment agents such as $FeCl_3$, $Fe_2(SO_4)_3$, chelate (e.g., trade name: Epolas MX-7, manufactured by Miyoshi Resin), or polymer heavy metal collector (e.g., trade name: Epoflock L-1, manufactured by Miyoshi Resin). However, an effective process for sewage treatment to remove the 6-valent selenium has not yet been found.

For this reason, when selenium (particularly the 6-valent selenium) contained in sewage, desulfurized sewage, etc., and is, for example, diluted with a large amount of water, an elaborate and costly back-end processing must be carried out to meet the above-mentioned standard for the dissolved amount.

SUMMARY OF THE INVENTION

Consequently, the first objective of the present invention is to provide a low-cost sewage process and apparatus which enables effective removal of selenium (especially the 6-valent selenium) and hence to meet the above-mentioned standard for the dissolved amount, and the like.

The second objective of the present invention is to provide a process for the treatment of sewage containing selenium, including microbioligical sewage treatment steps for the reduction of 6-valent selenium present in the sewage to 4-valent selenium and/or simple selenium, and to separate any resulting liquid from any solid that is present.

Another objective of the present invention is to carry out the microbiological treatment of the sewage by including a denitrification step and a selenium-reduction step using respectively, microorganisms with denitrification capability and activated sludge with selenium-reduction capability, to reduce the selenium from 6-valent selenium to 4-valent selenium and/or simple selenium.

A further objective of the present invention is to add an agent to separate the 4-valent selenium from the sewage.

An additional improvement is to add the agent to the sewage before or after the separating step and then carry out a second solid-liquid separation step.

Another improvement incorporating the principles of the present invention is to provide an apparatus for the treatment of sewage containing selenium (Se). Means for microbiological sewage treatment to reduce 6-valent selenium present in the sewage to 4-valent selenium and/or simple selenium as well as means for the separation of any resulting liquid from any present solid are included.

In an embodiment of the present invention, the means for microbiological treatment of sewage include means for denitrification and selenium reduction using microorganisms with denitrification capability and activated sludge with selenium-reduction capability to reduce the selenium from 6-valent selenium to 4-valent selenium and/or simple selenium substances.

BRIEF DESCRIPTION OF THE DRAWINGS

The above and other objectives, features and advantages of the present invention are clarified from the following detailed description and the accompanying drawings, referred as FIG. 1 and FIG. 2.

DESCRIPTION OF THE PREFERRED EMBODIMENTS

Figure 1:
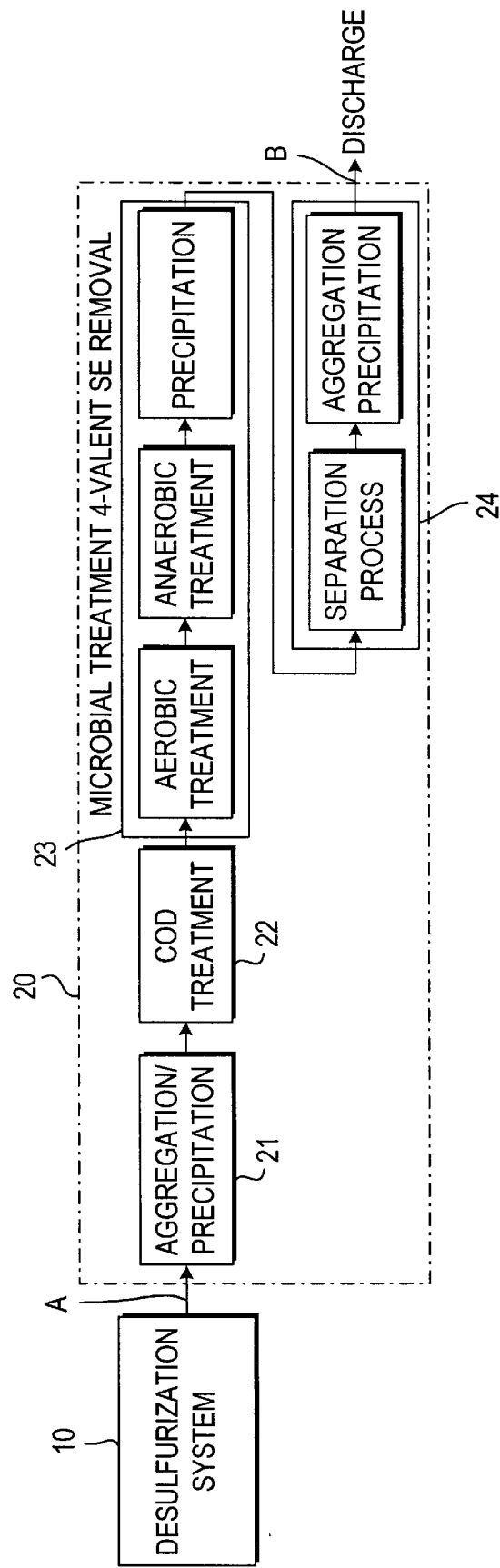
FIG. 1 represents a schematic block diagram of the apparatus for the first embodiment of the present invention.

In FIG. 1, the desulfurization system 10 is shown in block form since it is a conventional system. As an example the desulfurization system 10 is equipped with an absorber tower. Limestone slurry is supplied as absorbent to a tank at the bottom of the tower. The slurry in the tank is circulated in the absorber tower by means of circulation pumps. The circulated slurry enters in contact with the smog passing through the body of the tower, thus absorbing sulfur oxides contained in smog.

In the case of the "tank oxidation method," the absorbent slurry, after being in contact with the smog and circulated in the body of the tower, is oxidized by air entering the tank. Consequently, a solid gypsum is produced as a by-product in the tank. In this case, a part of the slurry contained in the tank is continuously discharged for solid-liquid separation. Gypsum with a low water content is continuously collected, while most of the separated water is recycled as limestone slurry make-up water.

In addition, a part of the separated water is discharged outside of the system as desulfurized discharged liquid A. This is a critical treatment in order to prevent slurry from affecting the desulfurization efficiency due to excess accumulation of impurities contained in the smog and dissolved into the circulated aqueous slurry. In the case of a coal-fired boiler, the desulfurized discharged water A, contains much selenium dissolved from the smog. For example, the selenium content of 6-valent selenium can be about 0.3 milligram per liter.

The desulfurized discharged water A is then applied to a sewage treatment apparatus 20 in accordance with the principles of this invention. The water is discharged as treated discharge water B after going through an aggregation and precipitation apparatus 21, COD treatment apparatus 22, a microbiological treatment apparatus 23, and the 4-valent selenium removal apparatus 24.

The aggregation and precipitation apparatus 21 performs the step of the process for which fine solid particles which could not be separated during the solid-liquid separation process for solid gypsum collection in the desulfurization system 10, are recovered. The COD apparatus 22 performs the step of the process for which organic contaminants are removed to maintain the COD under the standard value. This COD treatment step can be fulfilled by boiling the sewage at a high temperature to thermally crack the contaminants or by using a well-known method in which an adsorbent resin is used to selectively adsorb a specific contaminant.

Note that a part or all of the 4-valent selenium contained in the sewage reacts with an aggregation agent in the above-mentioned aggregation and precipitation apparatus 24, depositing selenite on the solid-phase side for removal. However, the 6-valent selenium at least is still dissolved in the sewage during its passage through the aggregation and precipitation apparatus 21 and the COD treatment apparatus 22, and is discharged downstream to the microbiological treatment apparatus 23.

In the microbiological treatment apparatus 23, each of the aerobic treatment (aerobic microbiological treatment), the anaerobic treatment (anaerobic microbiological treatment), and precipitation treatment (solid-liquid separation) takes place in this respective order. The aerobic treatment in the apparatus 23 employs an activated sludge which includes nitrous acid bacteria (the bacteria responsible for the oxidation of $NH_4$ to $NO_2^-$) and nitric acid bacteria (the bacteria responsible for the oxidation of $NO_2^-$ to $NO_3^-$). The sewage which has gone through the COD treatment apparatus 22 is introduced in the mixing or stirring tank. In this tank the activated sludge is floated or suspended by air which is pumped in as required (for sludge exposure to air).

In this aerobic treatment, the $NH_4$ in the sewage is oxidized in turn into $NO_2^-$ via nitrous acid bacteria in the activated sludge after a long time. Further, $NO_2^-$ is oxidized in turn into $NO_3^-$ via nitric bacteria in the activated sludge.

The sewage which has gone through this aerobic treatment undergoes a precipitation treatment as required, and is discharged from the downstream side (to the mixing tank used in anaerobic treatment described later) under conditions such as quantity of activated sludge for this aerobic treatment as little as possible is sent on to the anaerobic step.

Next, an anaerobic treatment step is performed in the apparatus 23 in which activated sludge is employed. The activated sludge includes microorganisms having a selenium-reduction capability from 6-valent selenium to 4-valent selenium and/or simple selenium, and denitrification bacteria (the bacteria which reduce $NO_3^-$ to produce $N_2$). The sewage which has gone through the above-mentioned aerobic treatment is introduced for stirring into the mixing tank in which the activated sludge is floated or suspended to supply nitritious salts such as acetate while maintaining the anaerobic environment.

In this anaerobic treatment, oxygen present in the $NO_3^-$ in sewage is reduced to produce $N_2$ via the denitrification bacteria in the activated sludge. Also oxygen in the 6-valent selenium (primary form: selenic acid $SeO_4^{2-}$) under discharge is reduced simultaneously via microorganisms having a selenium-reduction capability to reduce the selenium from 6-valent seleniuim to 4-valent selenium (primary form: selenious acid $SeO_3^{2-}$) or to further turn the 6-valent selenium into simple selenium.

In the precipitation portion of the microbiological treatment apparatus 23, the sewage which has undergone the above-mentioned anaerobic treatment is introduced to, for example, a precipitation separation apparatus, and the like, and is discharged downstream of it (the 4-valent selenium removal step) after sludge (solid) has been removed. At this time, generated $N_2$ is discharged to the atmosphere. In addition, most simple selenium deposits as sludge because its extremely low solubility. The 4-valent selenium deposits partly as sludge as well because its solubility is lower than that of the 6-valent selenium. For this reason, almost all the selenium, except some 4-valent selenium dissolved in the sewage, is taken into the sludge and removed from the sewage.

Note that the removed sludge via the precipitation treatment can be disposed as industrial waste. However, if a treatment agent which separates or elutes the 4-valent selenium is mixed with the sludge, and then dehydrated using a centrifugal precipitator and the like, a cake of sludge can be obtained for disposal. This is easy to handle and provides little problem with respect to selenium separation or elution.

In the 4-valent selenium removal apparatus 24, each of the separating or eluting treatments (the 4-valent selenium separation or eluting treatment) and the aggregation and precipitation treatment (solid-liquid separation) takes place in this respective order. The separating or eluting treatment employs the sewage which has undergone the above-mentioned microbacterial treatment step. This sewage is introduced into the mixing tank and mixed with an added treatment agent (e.g., compounds have 3-valent iron such as $FeCl_3$ or $Fe_2(SO_4)_3$) which separates or elutes the 4-valent selenium. With this treatment, the 4-valent selenium contained in the sewage (primary form: selenious acid $SeO_3^{2-}$) reacts with the conditioner represented, for example, by the reactions (1) and (2) or (3) and (4), detailed below, resulting in precipitated or eluted selenious acid iron ($Fe_2(SeO_3)_3$).

Chemical Reactions (1) $FeCl_3 \longrightarrow Fe^{3+} + 3Cl^-$ (2) $2Fe^{3+} + 3SeO_3^{2-} \longrightarrow Fe_2(SeO_3)_3 \downarrow$ or (3) $Fe_2(SeO_4)_3 \longrightarrow 2Fe^{3+} + 3SO_4^{2-}$ (4) $2Fe^{3+} + 3SeO_3^{2-} \longrightarrow Fe_2(SeO_3)_3 \downarrow$ For this reason, when the sewage is separated into solid and liquid in the aggregation and precipitation equipment 24, in the next aggregation and precipitation treatment, the 4-valent selenium is separated into a solid phase as selenious acid iron and is separated or eluted and mixed with the sludge for discharging. Therefore, the sewage B at discharge which has undergone the treatments in the sewage treatment apparatus contains little selenium and meets the aforementioned emission standard satisfactorily.

Note that the sludge removed from the aggregation and precipitation treatment can be disposed as industrial waste. However, if it is dehydrated using a centrifugal precipitator, one can obtain a cake of sludge for disposal, which is easy to handle. In the sludge, selenium is mostly in the separated or eluted state. Therefore, even when selenium is disposed in the form of a cake, the selenium elution standard is satisfactorily met.

As a consequence an example of adding an agent for separating or eluting the 4-valent selenium contained in the sewage whose sludge has been separated after undergoing microbiological treatment step has been so far described. It is also possible that the above-mentioned agent conditioner be added to the sewage before its sludge goes through the microbiological treatment step, and then the precipitated or eluted selenium be separated from the sludge in the solid-liquid separation step that follows.

According to the above-mentioned treatment, as will be reviewed in the example described below, the 6-valent selenium reduction from sewage, which conventionally was impossible, can be carried out to a satisfactory level, easily meeting the emission standard of 0.1 milligrams per liter. Also, because the 6-valent selenium reduction can take place simultaneously with denitrification, the equipment 23 configuration for the microbiological treatment (configuration for activated sludge removal) remains the same as it is for nitrification (aerobic) treatment and denitrification treatment. In this case, by only installing the equipment for the 4-valent selenium removal step, the process and apparatus incorporating the principles of the present invention can be easily and inexpensively utilized. In addition, compared to the process in which the 6-valent selenium reduction and denitrification takes place in separate steps, the process incorporating the principles of the present invention greatly shortens the total process time.

It is possible to manage the selenium concentration in the sewage, the microbiological treatment tank capacity, or the turnover conditions so that the 4-valent selenium removal step may not always be required. This is due to the fact that the selenium removal that occurs in the microbiological treatment step, which provides a lower selenium concentration for selenium (primarily the 4-valent selenium) left in the sewage may be less than the emission standard value.

Figure 2:
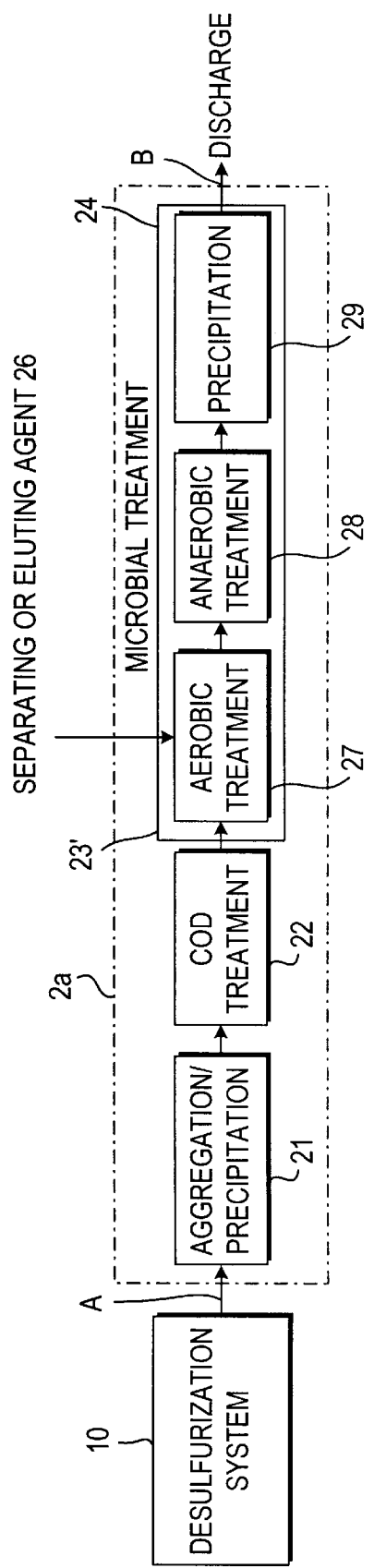
FIG. 2 corresponds to a schematic block diagram of apparatus for the second embodiment of the present invention.

Referring to FIG. 2, a second embodiment of the present invention will be described. In this embodiment, an agent or conditioner 26 which separates or elutes the 4-valent selenium is added and is mixed with sewage during the microbiological treatment step in the microbiological treatment apparatus 23'. The desulfurization system 10, the aggregation and precipitation apparatus 21, and the COD treatment apparatus 22 are the same as described for FIG. 1.

The agent or conditioner 26 (e.g., $FeCl_3$ or $Fe_2(SO_4)_3$, etc.) which separates or elutes the 4-valent selenium is added to a mixing tank 27 in the aerobic treatment as illustrated in FIG. 2 or to a mixing tank 28 in the anaerobic treatment.

The 4-valent selenium originally contained in the sewage and most of the 4-valent selenium reduced from the 6-valent selenium in the anaerobic treatment react with the agent or conditioner 26 represented, for example, by the aforementioned reactions (1) and (2) or (3) and (4). This produces precipitated or eluted selenious acid iron ($Fe_2(SeO_3)_3$) in the mixing tanks 27 and 28 in the aerobic and the anaerobic treatments, respectively, and further produces the 4-valent selenium which is separated or eluted for disposal or removal in the sludge produced from the subsequent precipitation treatment apparatus 29.

Therefore, the discharged sewage B which has undergone the treatments in the sewage treatment apparatus contains a small amount of selenium which meets the aforementioned emission standard satisfactorily. Also, in this example the 4-valent selenium removal step after the microbiological treatment is not required. The equipment configuration for the sewage treatment can remain the same as in the conventional configuration which does not have apparatus for a 4-valent selenium removal step. For this reason, the configuration of the equipment for sewage treatment can be very simple and the selenium removal function can be added without the cost of substantial additional equipment. Also, since the 4-valent selenium removal step is not required after microbiological treatment, this embodiment process of the present invention can greatly shorten the total process time.

Also, most of the separated or eluted selenium is in the sludge produced in the precipitation step during the microbiological treatment. This sludge can be made into a cake form via a solid-liquid separation step, if required, and selenium can be disposed of with little or no problem at all.

Note that the conditioner for separating or eluting the 4-valent selenium may contain 2-valent iron (e.g., $FeSO_4$). In this case also, the 2-valent iron results in 3-valent iron via the natural oxidation or forced oxidation in the aerobic treatment, causing the above-mentioned reactions (1) and (2) or (3) and (4) to occur.

A process incorporating the principles of this invention is described specifically referring to the examples mentioned herein. In order to put these examples into experimentation, a flue gas desulfurization system was used; the 6-valent selenium concentration in the activated sludge with denitrification bacteria used in the denitrification treatment was about 10 ppm; the activated sludge was kept in a sealed anaerobic environment for a culture period of 14 days. The microorganisms used for the denitrification bacteria were isolated and identified as belonging to the pseudomonas genus. More specifically, the bacteria belong to the aeruginosa species of the pseudomonas genus. Samples of such bacteria were deposited in accordance with the Budapest Treaty on Sep. 9, 1996 at the International Depositary Authority—National Institute of Bioscience and Human-Technology Agency of Industrial Science and Technology located at 1–3, Higashi 1-Chome Tsukuba, Ibaraki-Ken, 305, Japan and identified as pseudomanas sp. SR-34, FERM BP-5661 and SR-25, FERM BP-5662.

EXAMPLE NO. 1

A reduction experiment for the 6-valent selenium in sewage was conducted. The conditions of the experiment are shown in Table 1 below. 50 ml of the activated sludge and 450 ml of desulfurized sewage were mixed and stirred in a flask and sealed hermetically to make an anaerobic environment. After sealing, the mixture was kept under stirring condition for 24 hours at a temperature of 25° C., and then its solid part was left as a deposit. Only the supernatant fluid was taken and the concentration of the 6-valent selenium or the 4-valent selenium as well as the concentration of nitrogen ($NO_3^-$) in this fluid were measured. The results of the measurement are shown in Table 2.

TABLE 1

Test Conditions for the 6-Valent
Selenium Reduction Test Using Microorganisms

| Item | Concentration, etc. |
| --- | --- |
| Initial 6-valent selenium concentration | 0.31 mg / liter |
| Initial $NO_3^-$—N concentration | 204 mg / liter |
| Activated sludge concentration | 2,000 mg / liter |
| Liquid amount | 500 m liter |
| Temperature | 25° C. |
| Stirring | Yes |

TABLE 2

Results for the 6-Valent
Selenium Reduction Test Using Microorganisms

| Item | Concentration (mg / liter) |
| --- | --- |
| 6-valent selenium | 0.08 |
| 4-valent selenium | 0.10 |
| $NO_3^-$—N | <0.5 |

As shown in Table 2, the concentration of the 6-valent selenium was drastically lowered, while the concentration of the 4-valent selenium which was not measurable in the sewage before the treatment was increased.

When $FeCl_3$ was added to the supernatant liquor after the above treatment and was mixed and stirred, the resulting mixture was treated in an aggregation and precipitation treatment step, the resulting total selenium concentration was equal to 0.08 milligrams per liter, meeting the emission standard (0.1 milligrams per liter) satisfactorily.

EXAMPLE NO. 2

In this example, 50 ml of the activated sludge, 450 ml of desulfurized sewage (with a concentration of the 6-valent selenium: being 8 ppm) and 0.5 mg of $FeSO_4$ as a separation or eluent agent were mixed and stirred in a flask and sealed hermetically to make an anaerobic environment. The flask was sealed the mixture was kept under stirring conditions for 24 hours at 25° C. The sludge was precipitated while its supernatant liquor was collected; the concentration of the 6-valent selenium or the 4-valent selenium in the supernatant liquor was measured. As a result, no 6-valent selenium or 4-valent selenium was measured demonstrating little existence in the liquor. During this treatment, the pH was kept between 7 to 7.8.

It is clear that the process and apparatus incorporating the principles of the present invention should not be limited to the examples described above and other examples may also apply. For example, besides $FeCl_3$ or $Fe_2(SO_4)_3$, the following materials can be used as a separation agent or eluent for selenium: chelate (e.g., trade name: Epolas MX-7, manufactured by Miyoshi Resin), or polymer heavy metal collector (e.g., trade name: Epoflock L-1, manufactured by Miyoshi Resin). Also, as described before, the compounds having a 2-valent iron ($FeSO_4$) can be used as a separation agent.

Furthermore, as mentioned above, the 4-valent selenium reduction is not always required when the concentration of selenium (primarily the 4-valent selenium) remaining in the sewage after the microbiological treatment is less than the emission standard value. Also, the process and apparatus of sewage treatment incorporating the principles of the present invention can apply not only to desulfurization sewage but also to treatment of any other sewage having 6-valent selenium.

According to the above-described process and apparatus of sewage treatment, since selenium is reduced from the 6-valent selenium to the 4-valent selenium and/or simple selenium by means of the microbiological treatment, making the solid-liquid separation easier, much of the selenium may be removed as a sludge in this process. This is because the solubility of the simple selenium is extremely low and that of the 4-valent selenium is also lower than that of the 6-valent selenium. Therefore, it is possible to lower the concentration of the 6-valent selenium significantly, a situation impossible with a conventional process or apparatus.

To achieve the advantages of the present invention it is not necessary to make elaborate changes in conventional sewage treatment apparatus. The activated sludge must be changed. The removal of the 6-valent selenium can be carried out by conventional equipment utilizing this invention. Also, in this configuration, the total process time may be considerably shortened since the 6-valent selenium reduction and denitrification may take place in the same process step.

According to the above-described sewage treatment process, sewage treatment system configuration can be made easier because this process uses microorganisms with a denitrification capability and the activated sludge uses microorganisms with a selenium-reduction capability which reduces 6-valent selenium to 4-valent selenium and/or single selenium. Thus, the selenium reduction and denitrification takes place in the microbiological treatment apparatus at the same time. That is, for example, having separate steps for which the selenium reduction and denitrification use different sludges requires additional equipment specifically used for the selenium reduction (e.g., the mixing tank for the microorganisms treatment). However, the configuration of this invention intends to share a system. In other words, an existing sewage treatment system used conventionally for denitrification treatment by means of microorganisms, requiring no modification but just a different type of an activated sludge, yet can take advantage of the treatment and can perform the 6-valent selenium reduction. With this configuration, the selenium reduction and the denitrification takes place simultaneously, reducing the total process time required for sewage treatment.

The above-described process of sewage treatment removes 4-valent selenium which originally existed in sewage and which was produced from the reduction of 6-valent selenium by means of the sludge removal treatment (e.g., the precipitation treatment), because the microbiological treatment uses microorganisms having the denitrification capability and activated sludge having the selenium-reduction capability which changes the selenium from the 6-valent selenium to a 4-valent selenium and/or simple selenium substances. Therefore, the selenium concentration for all selenium in the sewage after treatment can be significantly lowered to meet an even more stringent standard value. In addition, this treatment is configured in such a way that further installation for the addition of a separation agent to a treatment tank enables the microbiological treatment, without requiring a mixing tank for separation agent and sewage mixing, thus reducing the capital cost for a sewage treatment system. This also provides easy modification of equipment which are currently used.

According to the above-described process of sewage treatment, by adding a separation agent to sewage after microbiological treatment for the removal of 4-valent selenium, most of the 4-valent selenium which originally existed in the sewage and which is the product of reduction of the 6-valent selenium during microbiological treatment can be precipitated and removed through the solid-liquid separation step. Therefore, the concentration of total selenium after the treatments can drop and meets the emission standard value satisfactorily.

After understanding the teachings of the present disclosure without departing from the scope thereof, various modifications will become possible for those skilled in the art.

What is claimed is:

1. A process for the treatment of sewage containing selenium (Se), comprising the step of microbiological treatment of sewage to reduce the 6-valent selenium present in the sewage to at least one of the group consisting of 4-valent selenium and simple selenium; and when a liquid and solid are present then utilizing a solid-liquid separation step for separating the resulting liquid from the solid that is present, said step of microbiological treatment of sewage using Pseudomonas sp. SR-34, FERM BP-5661.

2. A process for the treatment of sewage containing selenium (Se), comprising the step of microbiological treatment of sewage to reduce the 6-valent selenium present in the sewage to at least one of the group consisting of 4-valent selenium and simple selenium; and when a liquid and solid are present then utilizing a solid-liquid separation step for separating the resulting liquid from the solid that is present, said step of microbiological treatment of sewage using sp. SR-25, FERM BP-5662.

3. A process for the treatment of sewage containing 6 valent selenium (Se), comprising the steps of:

microbiological treatment of sewage with Pseudomonas sp. SR-34, FERM BP-5661 to reduce the 6-valent selenium present in the sewage to at least one of the group consisting of 4-valent selenium and simple selenium, and then, when a liquid and solid are present, utilizing a solid-liquid separation step for separating said resulting liquid from said solid.

4. A process for the treatment of sewage containing 6 valent selenium (Se), comprising the steps of:

microbiological treatment of sewage with Pseudomonas sp. SR-25, FERM BP-5662 to reduce the 6-valent selenium present in the sewage to at least one of the group consisting of 4-valent selenium and simple selenium, and then, when a liquid and solid are present, utilizing a solid-liquid separation step for separating said resulting liquid from said solid.

* * * * *